(12) United States Patent
Kumar et al.

(10) Patent No.: US 11,193,177 B2
(45) Date of Patent: Dec. 7, 2021

(54) PROCESS FOR RECOVERING HIGHER SUGAR FROM BIOMASS

(71) Applicants: Indian Oil Corporation Limited, Mumbai (IN); Department Of Biotechnology, New Delhi (IN)

(72) Inventors: Ravindra Kumar, Faridabad (IN); Surbhi Semwal, Faridabad (IN); Alok Satlewal, Faridabad (IN); Ravi Prakash Gupta, Faridabad (IN); Suresh Kumar Puri, Faridabad (IN); Sankara Sri Venkata Ramakumar, Faridabad (IN)

(73) Assignees: Indian Oil Corporation Limited, Mumbai (IN); Department of Biotechnology, New Delhi (IN)

( * ) Notice: Subject to any disclaimer, the term of this patent is extended or adjusted under 35 U.S.C. 154(b) by 267 days.

(21) Appl. No.: 16/452,243

(22) Filed: Jun. 25, 2019

(65) Prior Publication Data
US 2020/0002778 A1 Jan. 2, 2020

(30) Foreign Application Priority Data
Jun. 28, 2018 (IN) .............................. 201821024153

(51) Int. Cl.
| | |
|---|---|
| *C13K 1/02* | (2006.01) |
| *C12P 19/02* | (2006.01) |
| *C12P 19/14* | (2006.01) |
| *D21B 1/06* | (2006.01) |
| *D21B 1/36* | (2006.01) |
| *D21C 1/04* | (2006.01) |

(52) U.S. Cl.
CPC ................ *C13K 1/02* (2013.01); *C12P 19/02* (2013.01); *C12P 19/14* (2013.01); *D21B 1/061* (2013.01); *D21B 1/36* (2013.01); *D21C 1/04* (2013.01); *C12P 2201/00* (2013.01)

(58) Field of Classification Search
None
See application file for complete search history.

(56) References Cited

U.S. PATENT DOCUMENTS

| | | | |
|---|---|---|---|
| 5,627,269 A * | 5/1997 | Herak ................ | B01D 11/0219 536/2 |
| 7,932,063 B2 | 4/2011 | Dunson, Jr. et al. | |
| 2010/0268000 A1 | 10/2010 | Parekh et al. | |
| 2011/0300586 A1 | 12/2011 | Liu et al. | |
| 2011/0318796 A1 | 12/2011 | Walther | |
| 2014/0170713 A1 | 6/2014 | Retsina et al. | |
| 2014/0287076 A1 * | 9/2014 | Xing ...................... | A61K 36/21 424/776 |
| 2015/0090132 A1 * | 4/2015 | Poggenpohl .......... | B21C 23/211 100/35 |
| 2015/0329887 A1 * | 11/2015 | Wang ...................... | C12P 19/02 435/99 |
| 2018/0363017 A1 * | 12/2018 | Tolan ........................ | C12P 7/10 |

FOREIGN PATENT DOCUMENTS

WO WO-2013082616 A2 * 6/2013 .............. C12P 19/02

OTHER PUBLICATIONS

Kemppainen, Katariina, et al., "Hot water extraction and steam explosion as pretrealments for ethanol production from spruce bark", Bioresource Technology 117 (2012) 131-139.

* cited by examiner

*Primary Examiner* — Michelle F. Paguio Frising
(74) *Attorney, Agent, or Firm* — Melissa M. Hayworth; E. Joseph Gess

(57) ABSTRACT

An advantageous process for pre-treating lignocellulosic biomass to hydrolysable polysaccharide enriched biomass with reduced amount of inhibitors of catalysis comprising steps of: providing a feedstock comprising cellulosic biomass; chopping of cellulosic biomass to have a cellulosic biomass feed material of uniform size; feeding of uniform sized feed material to a horizontal counter current extraction unit; removing excess of water from the feed material obtained from the extraction unit; soaking the extruded feed material obtained from the extraction unit; optionally removing excess of water from the feed material obtained after acid soaking; steam pre-treating the feed material obtained after removing excess of water from the acid soaked feed material; neutralizing the slurry obtained from the steam pre-treating; and optionally saccharifying the neutralized slurry.

12 Claims, 2 Drawing Sheets

PROCESS FOR RECOVERING HIGHER SUGAR FROM BIOMASS

FIELD OF THE INVENTION

The present invention relates to an improved process for production of sugars and specifically for production of sugars from lignocellulosic biomass. More specifically, the present invention relates to an improved process for production of sugars from lignocellulosic biomass using a pre-treatment method that reduces the amount of inhibitors and improves the sugar conversion.

BACKGROUND OF THE INVENTION

There is increasing demand in generating potential and environmental sustainable alternative source to fossil reserves for the production of bio-ethanol and chemicals from plant derived lignocellulosic biomass. The bio-ethanol is produced from biomass by converting cellulose to sugar, fermenting sugars to ethanol, and then distilling and dehydrating the ethanol to create a high octane fuel that can substitute in whole or in part for gasoline.

In order to produce fermentable sugars from lignocellulosic biomass, it is essential to pre-treat the biomass for destruction of cell wall matrix and to make the biomass amenable to enzymatic hydrolysis. Subsequently enzymatic hydrolysis using cellulases leads to production of sugars, which upon fermentation using yeast results in the production of ethanol. Pre-treatment of lignocellulosic biomass is amongst the single, most expensive processing step. Therefore, development of a cost-effective and efficient biomass pre-treatment process remains one of the long-standing and unmet requirements in production of sugars and eventually biofuels from the lignocellulosic biomass.

A variety of physical, chemical, physicochemical and biological pre-treatment techniques have been explored to improve the accessibility of enzymes to cellulosic fibers. All these methodologies have been investigated by many researchers using different feedstocks and each of these has its own advantages and disadvantages.

Among all, steam explosion has been perceived as one of the most extensively operated pre-treatment due to relatively low cost. Under high pressure, water penetrates into the biomass, hydrates cellulose and removes hemicellulose and also partially removes lignin. The solubilization of hemicellulose is catalyzed by hydronium ions resulting from auto-ionization of water. It is reported to offer the advantages of efficiently decreasing particle size, disrupting plant cells resulting in an increased surface area and better accessibility of carbohydrates to enzymes and minimum corrosion of equipment due to mild pH of reaction media as compared to acid pre-treatment.

US 20100268000 discloses a process for efficient pre-treatment and conversion of lignocellulosic biomass to end-products with high conversion efficiency. It discloses pre-treatment of biomass by hot water extraction, exposure to acid and steam explosion.

US 20110300586 discloses a method of pre-treating lignocellulosic biomass comprising of two stages: hot water pre-treatment and acid treatment.

US 20110318796 discloses a method for preparing a hydrolysate containing soluble sugar molecules from biomass that contains cellulose and hemicellulose, wherein biomass is mechanically disintegrating in the presence of water; then liquid and solid disintegrated biomass is separated; solid biomass is then impregnated with an acid and treated with direct or indirect steam.

US 20140170713 discloses a fractionation processes for converting biomass into fermentable sugars, cellulose, and lignin. It discloses extraction of hemicelluloses from the feedstock in the presence hot water and acid treatment of solids obtained after extraction. Further it discloses hydrolyzing hemicelluloses to produce monomeric sugars.

Kemppainen et al in their study "Hot water extraction and steam explosion as pre-treatments for ethanol production from spruce bark", (Bioresource Technology 117:131-9 Apr. 2012) discloses three pre-treatment methods and provide their comparison, wherein pre-treatment methods are steam explosion (SE), hot water extraction (HWE), and sequential hot water extraction and steam explosion (HWE+SE).

U.S. Pat. No. 7,932,063 discloses a method for obtaining fermentable sugars from biomass, wherein fermentable sugars are obtained by pre-treating biomass under conditions of high solids and low ammonia concentration, followed by saccharification.

The inventors of the present application have developed an improved process for pre-treating lignocellulosic biomass that reduces the amount of inhibitors and improves the production/recovery/conversion of sugars from lignocellulosic biomass.

SUMMARY OF THE INVENTION

The present invention provides a process for production of sugars from lignocellulosic biomass using a pre-treatment method that reduces the amount of inhibitors and improves the production/recovery/conversion of sugars from lignocellulosic biomass.

In another embodiment, the invention provides a process for pre-treating lignocellulosic biomass that reduces the amount of inhibitors and improves the production/recovery/conversion of sugars from lignocellulosic biomass.

In another embodiment, the invention provides a process for pre-treating lignocellulosic biomass to a hydrolysable polysaccharide enriched biomass comprising providing a feedstock of cellulosic biomass.

In another embodiment, the invention provides a process for pre-treating lignocellulosic biomass to a hydrolysable polysaccharide enriched biomass comprising chopping of cellulosic biomass using knife-mill to have a cellulosic biomass feed material of size in the range of 1 mm to 40 mm.

In another embodiment, the invention provides a process for pre-treating lignocellulosic biomass to a hydrolysable polysaccharide enriched biomass comprising feeding of chopped feed material to a horizontal counter current extraction unit through one end.

In another embodiment, the invention provides a process for pre-treating lignocellulosic biomass to a hydrolysable polysaccharide enriched biomass comprising removing excess of water from the feed material obtained from the horizontal counter current extraction unit.

In another embodiment, the invention provides a process for pre-treating lignocellulosic biomass to a hydrolysable polysaccharide enriched biomass comprising acid soaking the feed material obtained after removing excess of water from the feed material obtained from the horizontal counter current extraction unit.

In another embodiment, the invention provides a process for pre-treating lignocellulosic biomass to a hydrolysable polysaccharide enriched biomass comprising optionally removing excess of water from the acid soaked feed material.

In another embodiment, the invention provides a process for pre-treating lignocellulosic biomass to a hydrolysable polysaccharide enriched biomass comprising steam pre-treating the feed material obtained after removing excess of water from the acid soaked feed material.

In another embodiment, the invention provides a process for pre-treating lignocellulosic biomass to a hydrolysable polysaccharide enriched biomass comprising neutralizing the slurry obtained from the steam pre-treating the feed material.

In another embodiment, the invention provides a process for pre-treating lignocellulosic biomass to a hydrolysable polysaccharide enriched biomass comprising saccharifying the neutralized slurry obtained from the steam pre-treating the feed material.

In another embodiment, the invention provides a process for pre-treating lignocellulosic biomass to a hydrolysable polysaccharide enriched biomass comprising steps of:

a) providing a feedstock comprising cellulosic biomass;
b) chopping of cellulosic biomass using knife-mill to have a cellulosic biomass feed material of size in the range of 1 mm to 40 mm;
c) feeding of feed material obtained from the preceding step b) in to a horizontal counter current extraction unit through one end;
d) removing excess of water from the feed material obtained from the preceding step c);
e) acid soaking the feed material obtained from the preceding step d);
f) optionally removing excess of water from the feed material obtained from preceding step e);
g) steam pre-treating the feed material obtained from the preceding step f);
h) neutralizing the slurry obtained from the preceding step g); and
i) optionally saccharifying the neutralized slurry obtained from the preceding step h).

In still another embodiment, the invention provides a process for pre-treating lignocellulosic biomass to a hydrolysable polysaccharide enriched biomass, wherein a hot water is simultaneously introduced in to a horizontal counter current extraction unit from the other end while introducing feed material from the one end.

In still another embodiment, the invention provides a process for pre-treating lignocellulosic biomass to a hydrolysable polysaccharide enriched biomass, wherein the temperature of hot water introduced in to a horizontal counter current extraction unit is in the range of 70 to 90° C.

In still another embodiment, the invention provides a process for pre-treating lignocellulosic biomass to a hydrolysable polysaccharide enriched biomass, wherein feed material is treated for 5 to 120 minutes in horizontal counter current extraction unit.

In still another embodiment, the invention provides a process for pre-treating lignocellulosic biomass to a hydrolysable polysaccharide enriched biomass, wherein removal of excess water from feed material after processed in horizontal counter current extraction unit is carried out by hydraulic extrusion.

In still another embodiment, the invention provides a process for pre-treating lignocellulosic biomass to a hydrolysable polysaccharide enriched biomass, wherein the acid soaking is carried out in a 1 to 2% acid solution and wherein acid is selected from sulphuric acid, nitric acid and phosphoric acid.

In still another embodiment, the invention provides a process for pre-treating lignocellulosic biomass to a hydrolysable polysaccharide enriched biomass, wherein the acid soaking is carried out using sulphuric acid for 5 to 120 minutes at the room temperature.

In still another embodiment, the invention provides a process for pre-treating lignocellulosic biomass to a hydrolysable polysaccharide enriched biomass, wherein the excess water after acid soaking is optionally removed by using hydraulic press.

In still another embodiment, the invention provides a process for pre-treating lignocellulosic biomass to a hydrolysable polysaccharide enriched biomass, wherein the steam pre-treating of the feed material is carried using a steam explosion at a temperature of 150 to 200° C., for a residence time of 1 to 30 minutes, at a pressure of 5 to 30 bar and at a pH 3 to 5.

In still another embodiment, the invention provides a process for pre-treating lignocellulosic biomass to a hydrolysable polysaccharide enriched biomass, wherein the neutralization of slurry is carried out using ammonia solution.

In still another embodiment, the invention provides a process for pre-treating lignocellulosic biomass to a hydrolysable polysaccharide enriched biomass, wherein the saccharification of pre-treated lignocellulosic biomass is carried out using enzymes.

In still another embodiment, the invention provides a process for pre-treating lignocellulosic biomass to a hydrolysable polysaccharide enriched biomass, wherein the saccharification is carried out using cellulases.

In still another embodiment, the invention provides a process for pre-treating lignocellulosic biomass to a hydrolysable polysaccharide enriched biomass, wherein treatment in horizontal counter current extraction and acid soaking are carried out for 60 minutes.

In still another embodiment, the invention provides a process for pre-treating lignocellulosic biomass to a hydrolysable polysaccharide enriched biomass, wherein the excess water is removed after processing feed material in horizontal counter current extraction to have a solid-liquid ratio of around 1:1.

In still another embodiment, the invention provides a process for pre-treating lignocellulosic biomass to a hydrolysable polysaccharide enriched biomass, wherein the excess water is removed after acid soaking to have a solid-liquid ratio of around 1:1.

DESCRIPTION OF THE ACCOMPANYING DRAWINGS

FIG. 1A-C shows the time course of glucan conversion at different enzyme concentrations for different pre-treated biomass samples obtained from different pre-treatment processes.

DETAILED DESCRIPTION OF THE INVENTION

Figure 1A:
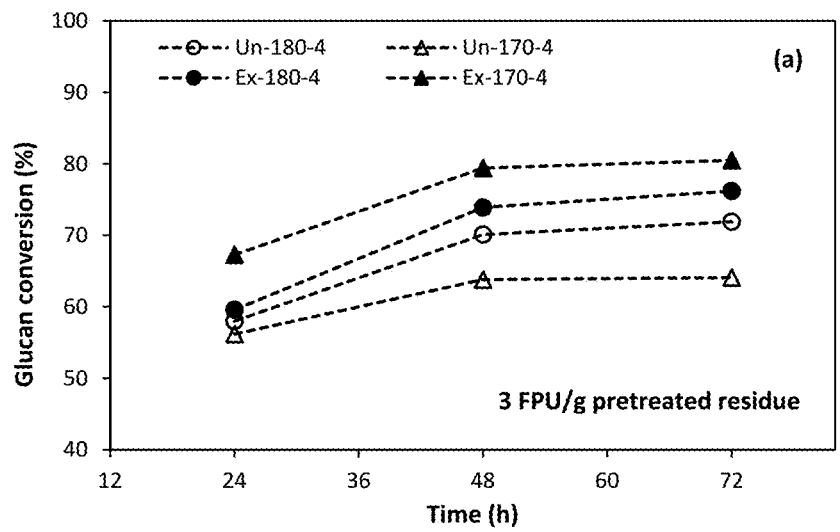
FIG. 1A shows a percentage of glucan conversion when cellulase (Ctec-3) is used at a concentration of 3 FPU/g of the biomass.

The present invention provides a process for production of sugars from lignocellulosic biomass using a pre-treatment method that reduces the amount of inhibitors and improves the production/recovery/conversion of sugars from lignocellulosic biomass. In the process a feedstock comprising cellulosic biomass is chopped to have a feed material of a uniform size in the range of 1 mm to 40 mm using knife-mill and is fed in to the horizontal counter current extraction unit through one end and a hot water from the other end at 70 to 90° C. temperature for 5 to 120 minutes and preferably for 60 minutes. The biomass obtained after treatment in horizontal counter current extraction unit is subjected to an extruder to remove water and is then subjected to soaking in dilute sulphuric acid and is fed into the pre-treatment reactor after dewatering. Pre-treated biomass is then neutralized and hydrolysed using enzymes to get fermentable sugars. In the process the biomass feed material was extruded to remove excess water by hydraulic extrusion. Further, the extruded biomass feed material was soaked in 1 to 2% of acid solution at room temperature for 5 to 120 minutes and preferably for 60 minutes and the soaked feed material is optionally dewatered by hydraulic press. Thereafter, the extruded and soaked biomass feed material was then pre-treated by steam explosion at 150 to 200° C. for residence time of 1 to 30 min at a pressure of 5 to 30 bar at pH 3 to 5 and a slurry received after steam explosion of feed material is neutralized using ammonia solution and is enzymatically saccharified using cellulases.

The present invention discloses an improved pre-treatment method of lignocellulosic biomass producing lower amount of inhibitors and thereby improving the sugar conversion. The process of present invention improves removal of extractives by hot water treatment followed by acid soaking prior to steam explosion, which improve the sugar conversion, reduces the enzyme dosage required for hydrolysis, hydrolysis time and overall process efficiency.

In accordance with the present invention, the process comprises the steps of pre-treatment of biomass with hot water extraction for a period of 5 to 120 minutes, impregnation by dilute sulphuric acid followed by steaming at high temperature and pressure. The biomass slurry so obtained is further treated with a cocktail of saccharification enzyme after neutralization with ammonia solution to produce fermentable sugars.

The present invention provides a process for pre-treating lignocellulosic biomass to hydrolysable polysaccharide enriched biomass comprising steps of:
(a) Providing a feedstock comprising cellulosic biomass;
(b) Biomass was chopped to have a the feed material having uniform size in the range of 1 mm to 40 mm using knife-mill;
(c) The chopped biomass feed material was fed in to the horizontal counter current extraction unit through one end and hot water from the other end at 70 to 90° C. temperature for 5 to 120 minutes and preferably for 60 minutes;
(d) The Biomass feed material thus received was extruded to remove excess water by hydraulic extrusion;
(e) The extruded biomass feed material was soaked in 1 to 2% of acid solution at room temperature for 5 to 120 minutes and preferably for 60 minutes;
(f) The soaked feed material is optionally dewatered by hydraulic press.
(g) The extruded and soaked biomass feed material was then pre-treated by steam explosion at 150 to 200° C. for residence time of 1 to 30 min at a pressure of 5 to 30 bar at pH 3 to 5.
(h) Slurry received after steam explosion of feed material was neutralized using ammonia solution.
(i) Neutralized slurry was enzymatically saccharified using cellulases.

In the present invention, removal of extractives by hot water followed by acid soaking prior to steam explosion improves the sugar conversion, reduces the enzyme dosage required for hydrolysis, hydrolysis time and overall process efficiency. In addition, further improvement is achieved by subjecting the biomass to a squeezing or compression steps to extract toxic impurities, which improve catalyst and water impregnation after the steam explosion step.

Intermediate removal of excess water using hydraulic extrusion and or hydraulic press improves the results of pre-treatment processes. The described herein also brings the biomass to a same set of conditions prior to pre-treatment which is important for consistent results. The process described herein provide the feed material with soften fibers with even distribution of moisture necessary for uniform catalysis.

Following non-limiting examples are given by way of illustration for specific embodiments thereof and therefore should not be construed to limit the scope of the invention.

EXAMPLES

Example 1

The rice straw (RS) was milled through a 10 mm mesh screen using a knife mill. Air-dried rice straw was stored in plastic bags at room temperature for further use. The chemical composition of this rice straw was; cellulose 36.7%, hemicellulose 21.3%, acetyl content 1.3%, lignin 12.5% and ash 12.0%.

3 Kg rice straw (dry weight) was soaked in 1% (w/w) of acid solution with a solid to liquid ratio maintained as 1:19 in a 100 L stainless steel (SS) container at room temperature for 1 hour with an intermittent manual stirring. The soaked rice straw was dewatered using a pneumatic hydraulic press at 100 bar for 15 min to get about 1:1 solid-liquid ratio. The pressed and squeezed solid (0.45 kg) so obtained was subjected to steam explosion at a temperature of 180° C. for residence time of 4 minutes. Steam explosion pilot plant comprising of a high pressure and high-temperature reactor made of stainless steel of 10 L capacity equipped with feeding hopper, cyclone separator, quick opening pneumatic butterfly valve, steam boiler and a noise absorber. Before starting the experiments, steam explosion digester was flushed 2 to 3 times with steam of 10 to 15 bar to quickly attain the desired operating temperature in actual experiments. After completion of the reaction, the ball valve was opened leading to rapid explosive decompression and breakdown of the biomass residue. The treated residue was recovered from cyclone separator. For each set of experiment 5 explosions were consecutively conducted and pre-treated rice straw feed material slurry was collected from the cyclone separator so as to minimize the error.

After the steam explosion, a small representative portion of the pre-treated slurry was withdrawn and total solids (TS) in slurry are determined by the NREL method (NREL/TP-510-42621). Thereafter, the solid fraction after washing was taken as water insoluble solids (WIS) determined by the NREL method (NREL/TP-510-42627). Whereas, water soluble (WS) sugars and inhibitors were calculated by measuring their concentration in the liquid portion by HPLC using NREL protocol (NREL/TP-510-42623) and the data obtained is given herein in Table 1. The TS and WIS were calculated by using the following equation:

$$\% \text{ Total solids } (TS) = \frac{\text{Weight}_{dry\ sample}}{\text{Weight}_{sample\ as\ recieved}} * 100 \qquad \text{Equation 1}$$

$$\% \text{ Water insoluble solids } (WIS) = \frac{ODW_{washed\ solids}}{ODW_{slurry}} * 100 \qquad \text{Equation 2}$$

Compositional analysis of cellulose rich residue is performed by using two stage acid hydrolysis method following a standard protocol of NREL (NREL/TP-510-42618) and the data obtained is presented in Table 2. The pre-treated residue received was found to have solid content of 65%. After steam explosion pre-treatment the glucan content increased from 36.7 to 52.5% whereas, xylan content decreased from 21.3 to 5.5%.

Solid part, i.e. cellulose rich residue obtained after pre-treatment was used as such without washing and neutralizing by using ammonia solution to maintain the pH of 5.0 to 5.3. The neutralized slurry was subjected to enzymatic hydrolysis at 15% TS (total solids). 15.0 g of pre-treated biomass (oven dry weight, ODW) were taken in 500 mL erlenmeyer flasks and suspended in 0.05 M sodium citrate buffer (pH 5.0) making final volume upto 100 ml. The mixture was pre-incubated at 50° C. for 30 min followed by adding Ctec-3 enzyme of 3, 4 and 5 FPU/g of TS. The mixture was incubated in an orbital shaker at 50° C. up to 72 h at 200 rpm. The samples were withdrawn at varying intervals and heated at 80° C. for 5 min to denature the enzyme followed by centrifugation (8000 g for 10 min). The samples were filtered using 0.45 μm filter and analyzed for sugars by HPLC (NREL/TP-510-42618). The glucan conversion was calculated by using following equation:

$$\text{Glucan hydrolysis \%} = \frac{\text{Glucose (g) released in enzymatic hydrolysis}}{\text{Glucose (g) in the pretreated } RS} * 1.11 * 100 \qquad \text{Equation 3}$$

Figure 1B:
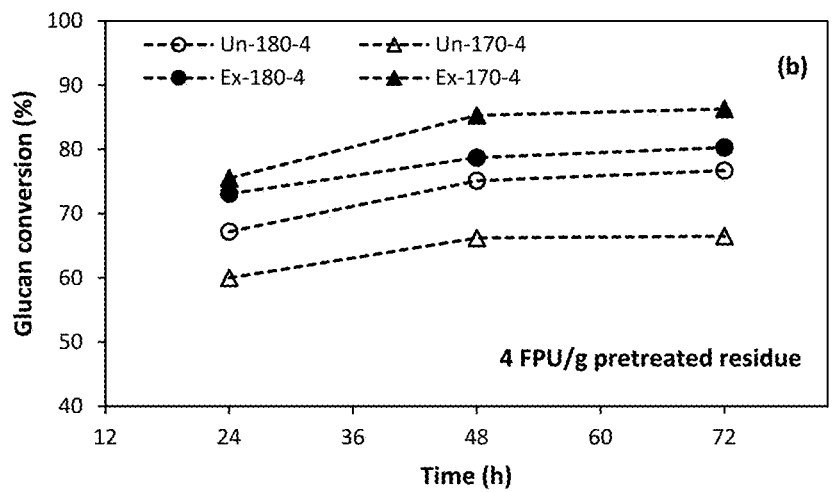
FIG. 1B shows a percentage of glucan conversion when cellulase (Ctec-3) is used at a concentration of 4 FPU/g of the biomass.
Figure 1C:
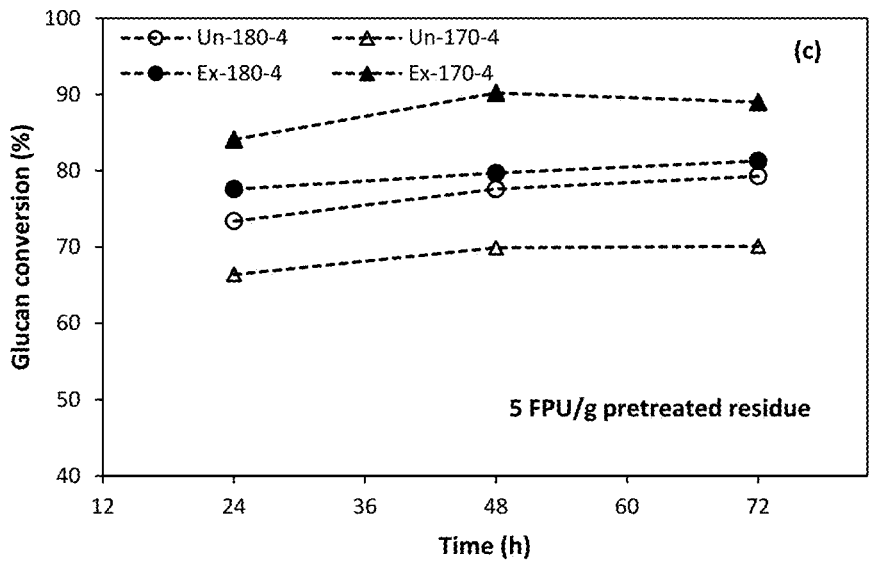
FIG. 1C shows a percentage of glucan conversion when cellulase (Ctec-3) is used at a concentration of 5 FPU/g of the biomass.
Figure 2:
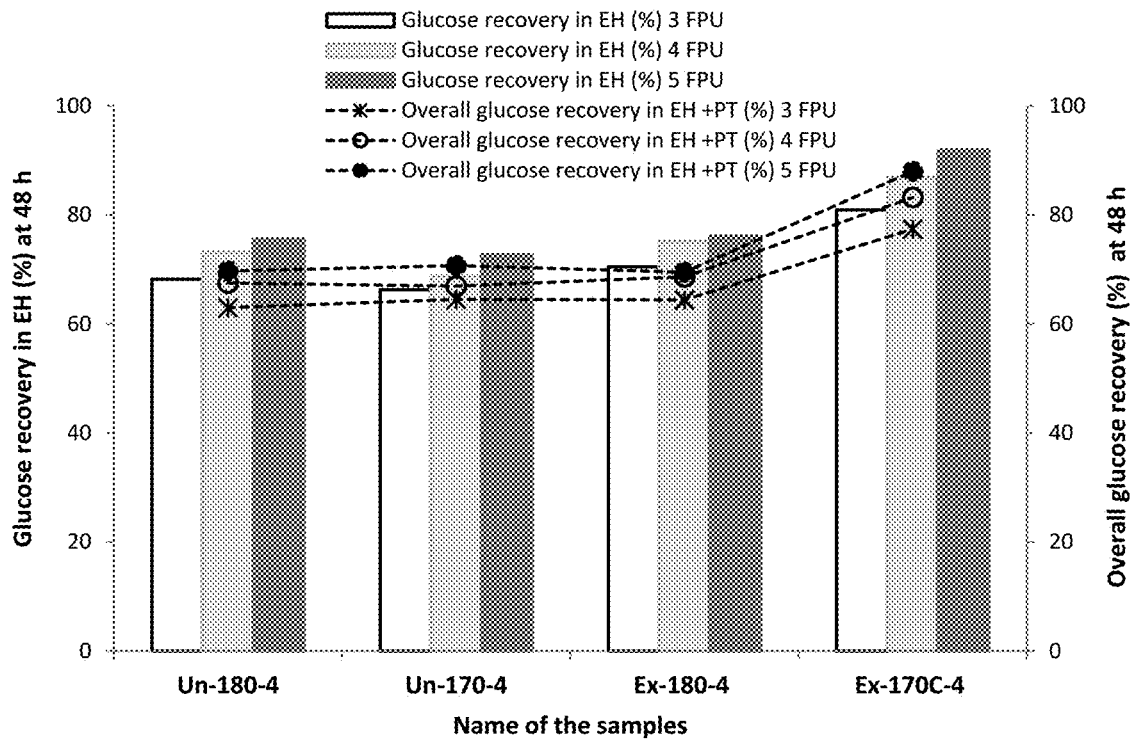
FIG. 2 illustrate the glucose recovery in enzymatic hydrolysis at 48 h and overall glucose recovery in enzymatic hydrolysis (48 h) and pre-treatment (after steam explosion) of different biomass at different enzyme dosages.

The time course of glucan hydrolysis of the pre-treated residue with different enzyme dosage using 15% loading is shown in FIG. 1. FIG. 2 shows the glucose recovery (glucose from enzymatic hydrolysis) and overall glucose recovery (glucose from enzymatic hydrolysis+pretreatment step) of different pre-treated residue after steam explosion.

Example 2

The feedstock used in this experiment was same as used in example 1 i.e. rice straw. The experiment was performed in similar conditions as described in example 1 except for steam explosion temperature, which is carried out at a temperature of 170° C.

The pre-treated residue received was found to have solid content of 66.6%. After steam explosion the glucan content increased from 36.7 to 54.7% whereas, xylan content decreased from 21.3 to 5.8%.

Example 3

The rice straw (RS) was milled through a 10 mm mesh screen using a knife mill. Air-dried rice straw was stored in plastic bags at the room temperature for further use. The chemical composition of this rice straw was given in Example 1.

3 Kg rice straw (dry weight) was fed into the horizontal counter current extraction unit through one end and hot water from the other end at a rate of 3 kg h$^{-1}$ with temperature of 80 to 90° C. for 60 minutes. The biomass to water ratio was 1:12. The biomass thus received was extruded to remove excess water using hydraulic press at pressure of up to 100 bar for 5 to 10 min to get about 1:1 solid-liquid ratio. The extracted rice straw was then soaked in 1% (w/w) of acid solution with a solid-liquid ratio maintained as 1:19 in a 100 L stainless steel (SS) container at room temperature for 1 hour with an intermittent manual stirring. The soaked rice straw was dewatered using a pneumatic hydraulic press at 100 bar for 15 min to get about 1:1 solid-liquid ratio. The pressed and squeezed solid (0.45 kg) so obtained was subjected to steam explosion at a temperature of 180° C. for residence time of 4 minutes. Steam explosion pilot plant comprising of a high pressure and high-temperature reactor made of stainless steel of 10 L capacity equipped with feeding hopper, cyclone separator, quick opening pneumatic butterfly valve, steam boiler and a noise absorber. Before starting the experiments, steam explosion digester was flushed 2 to 3 times with steam of 10 to 15 bar to quickly attained the desired operating temperature in actual experiments. After completion the reaction, the ball valve was opened leading to rapid explosive decompression and breakdown of the biomass residue. The treated residue was recovered from cyclone separator.

For each set of experiment 5 explosions were consecutively conducted and pre-treated straw feed material slurry was collected from the cyclone separator so as to minimize the error and get high solid/liquid ratio.

After the steam explosion, a small representative portion of the pre-treated slurry was withdrawn and total solids (TS) in slurry are determined by the NREL method (NREL/TP-510-42621). Thereafter, the solid fraction after washing was taken as water insoluble solids (WIS) determined by the NREL method (NREL/TP-510-42627). Whereas, water soluble (WS) sugars and inhibitors were calculation by measuring their concentration in the liquid portion by HPLC using NREL protocol (NREL/TP-510-42623) and the data obtained is given in Table 1. The TS and WIS were calculated by using the following equation:

$$\% \text{ Total solids } (TS) = \frac{\text{Weight}_{dry\ sample}}{\text{Weight}_{sample\ as\ recieved}} * 100 \qquad \text{Equation 1}$$

$$\% \text{ Water insoluble solids } (WIS) = \frac{ODW_{washed\ solids}}{ODW_{slurry}} * 100 \qquad \text{Equation 2}$$

Compositional analysis of cellulose rich residue is performed by using two stage acid hydrolysis method, following a standard protocol of NREL (NREL/TP-510-42618) and the data is obtained is presented in Table 2. The pre-treated residue received was found to have solid content of 70.6%. After steam explosion pre-treatment the glucan content increased from 36.7 to 51.0% whereas, xylan content decreased from 21.3 to 4.2%.

Solid part, i.e. cellulose rich residue obtained after pre-treatment was used as such without washing and neutralizing with ammonia solution to maintain the pH of 5.0 to 5.3. The neutralized slurry was subjected to enzymatic hydrolysis at 15% TS (total solids). 15.0 g of pre-treated biomass (oven dry weight, ODW) were taken in 500 mL erlenmeyer flasks and suspended in 0.05 M sodium citrate buffer (pH 5.0) making final volume upto 100 ml. The mixture was pre-incubated at 50° C. for 30 min followed by adding Ctec-3 enzyme of 3, 4 and 5 FPU/g of TS. The mixture was incubated in an orbital shaker at 50° C. up to 72 h at 200 rpm. The samples were withdrawn at varying intervals and heated at 80° C. for 5 min to denature the enzyme followed by centrifugation (8000 g for 10 min). The samples were filtered using 0.45 μm filter and analyzed for sugars by HPLC (NREL/TP-510-42618). The glucan conversion was calculated by using following equation:

$$\text{Glucan hydrolysis \%} = \frac{\text{Glucose (g) released in enzymatic hydrolysis}}{\text{Glucose (g) in the pretreated } RS} *1.11*100 \quad \text{Equation 3}$$

The time course of glucan hydrolysis of the pre-treated residue with different enzyme dosage using 15% loading is shown in FIG. 1. FIG. 2 shows the glucose recovery (glucose from enzymatic hydrolysis) and overall glucose recovery (glucose from enzymatic hydrolysis+pretreatment step) of different pre-treated residue after steam explosion.

Example 4

Rice straw was taken as raw material and the experiment was carried out in similar condition as explained for example 3 except that the steam explosion temperature is 170° C.

The pre-treated residue received was found to have solid content of 68.0%. After steam explosion pre-treatment the glucan content increased from 36.7 to 56.5% whereas, xylan content decreased from 21.3 to 4.5%.

We claim:

1. A process for pre-treating lignocellulosic biomass to hydrolyzable polysaccharide enriched biomass comprising steps of:
   a. providing a feedstock comprising cellulosic biomass;
   b. chopping of cellulosic biomass using knife-mill to have a cellulosic biomass feed material of size in the range of 1 mm to 40 mm;
   c. feeding of feed material obtained from the preceding step b) in to a horizontal counter current extraction unit through one end and simultaneously introducing hot water into said horizontal counter current extraction unit from the other end;
   d. removing excess water from the feed material obtained from the preceding step c) by hydraulic extrusion;
   e. soaking the feed material obtained from the preceding step d) in a 1 to 2% acid solution;
   f. removing excess water from the feed material obtained from preceding step e) by hydraulic extrusion;
   g. steam pre-treating the feed material obtained from the preceding step f);
   h. neutralizing the slurry obtained from the preceding step g); and
   i. saccharifying the neutralized slurry obtained from the preceding step h).

2. The process as claimed in claim 1, wherein the temperature of hot water introduced in to a horizontal counter current extraction unit in step c) is in the range of 70 to 90° C.

3. The process as claimed in claim 1, wherein step c) is carried out for 5 to 120 minutes.

4. The process as claimed in claim 1, wherein the soaking in step e) is carried out in an acid solution selected from the group consisting of sulfuric acid, nitric acid and phosphoric acid.

TABLE 1

Amount of water soluble (WS) sugars and inhibitors present in the pre-treated biomass obtained from different pre-treatment processes

| Experiments | Pre-treatment conditions [Un/Ex-T-t][a] | WIS (%) | TS (%) | Pre-treatment Hydrolysate (g/L) | | | | | | | |
|---|---|---|---|---|---|---|---|---|---|---|---|
| | | | | Cellobiose | Glucose | Xylose | Arabinose | Formic acid | Acetic Acid | HMF | Furfural |
| Exp-1 | Un-180-4 | 65.0 | 16.1 | 0.6 | 2.5 | 26.3 | 4.8 | 0.1 | 0.1 | 0.8 | 0.1 |
| Exp-2 | Un-170-4 | 66.6 | 16.7 | 0.0 | 2.4 | 25.1 | 5.2 | 0.0 | 0.4 | 0.1 | 0.2 |
| Exp-3 | Ex-180-4 | 70.6 | 18.0 | 0.7 | 3.9 | 36.1 | 5.2 | 0.2 | 0.2 | 1.1 | 0.2 |
| Exp-4 | Ex-170-4 | 68.0 | 18.1 | 0.0 | 3.2 | 34.0 | 5.5 | 0.0 | 0.6 | 0.1 | 0.6 |

[a]Un/Ex, T and t refers to native rice straw followed by dilute acid soaked (Un) or extruded rice straw followed by dilute acid soaked (Ex); pretreatment temperature (° C.) and residence time (min) respectively.

TABLE 2

Compositional analysis of residual biomass obtained from different pre-treatment processes

| Experiments | Pre-treatment conditions [RS/T/t][a] | Chemical composition of pretreated biomass (%) | | | | | | Removal during Pre-treatment (%) | |
|---|---|---|---|---|---|---|---|---|---|
| | | Glucan | Xylan | Acetyl content | lignin | Ash | Extractives | Xylan | lignin |
| | Native | 36.7 | 21.3 | 1.3 | 12.5 | 12.0 | 16.1 | N/A | N/A |
| Exp-1 | Un-180-4 | 52.5 | 5.5 | 0.5 | 24.4 | 17.1 | 0 | 83.2 | −26.9 |
| Exp-2 | Un-170-4 | 54.7 | 5.8 | 0 | 22.6 | 16.9 | 0 | 81.9 | −20.4 |
| Exp-3 | Ex-180-4 | 51.0 | 4.2 | 0.2 | 25.5 | 19.1 | 0 | 86.1 | −44.0 |
| Exp-4 | Ex-170-4 | 56.5 | 4.5 | 0 | 21.1 | 18 | 0 | 85.6 | −14.8 |

5. The process as claimed in claim 1, wherein the step e) is carried out in a 1 to 2% sulfuric acid for 5 to 120 minutes at the room temperature.

6. The process as claimed in claim 1, wherein the steam pre-treating of the feed material in step g) is carried using a steam explosion at a temperature of 150 to 200° C., for a residence time of 1 to 30 minutes, at a pressure of 5 to 30 bar and at a pH of 3 to 5.

7. The process as claimed in claim 1, wherein the neutralization of slurry in step h) is carried out using ammonia solution.

8. The process as claimed in claim 1, wherein the saccharification in step i) is carried out using enzymes.

9. The process as claimed in claim 8, wherein the enzymes are cellulases.

10. The process as claimed in claim 1, wherein step c) and step e) are carried out for 60 minutes.

11. The process as claimed in claim 1, wherein step d) and step f) are carried out to obtain a feed material having a solid-liquid ratio of around 1:1.

12. A process for the production of sugars from lignocellulosic biomass using a pre-treatment method as claimed in claim 1, wherein the concentration of cellulosic enzyme inhibitors is significantly reduced to improve the production/recovery/conversion of sugars from lignocellulosic biomass as compared to a method having one pretreatment.

\* \* \* \* \*